United States Patent
Jiang

(10) Patent No.: US 11,400,096 B2
(45) Date of Patent: Aug. 2, 2022

(54) SMALL MOLECULES FOR THE TREATMENT OF AUTOIMMUNE DISORDERS

(71) Applicant: Jean X. Jiang, San Antonio, TX (US)

(72) Inventor: Jean X. Jiang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 167 days.

(21) Appl. No.: 16/757,021

(22) PCT Filed: Oct. 19, 2018

(86) PCT No.: PCT/US2018/056666
§ 371 (c)(1),
(2) Date: Apr. 17, 2020

(87) PCT Pub. No.: WO2019/079691
PCT Pub. Date: Apr. 25, 2019

(65) Prior Publication Data
US 2021/0361660 A1   Nov. 25, 2021

Related U.S. Application Data

(60) Provisional application No. 62/574,329, filed on Oct. 19, 2017.

(51) Int. Cl.
*A61K 31/522* (2006.01)
*A61K 31/52* (2006.01)

(52) U.S. Cl.
CPC ............ *A61K 31/522* (2013.01); *A61K 31/52* (2013.01)

(58) Field of Classification Search
CPC .... C07D 473/06; C07D 473/34; A61K 31/52; A61K 31/522; A61P 29/00
USPC ................... 544/268, 277; 514/263.2, 263.4
See application file for complete search history.

(56) References Cited

U.S. PATENT DOCUMENTS

| | | |
|---|---|---|
| 2005/0245546 A1 | 11/2005 | Cristalli |
| 2006/0116412 A1 | 6/2006 | Ng |
| 2008/0176815 A1 | 7/2008 | Meutermans et al. |
| 2009/0215727 A1 | 8/2009 | Douglas |
| 2013/0123280 A1 | 5/2013 | Kalla et al. |
| 2014/0206702 A1 | 7/2014 | Lai |

FOREIGN PATENT DOCUMENTS

| | | |
|---|---|---|
| WO | WO 2009/088518 | 7/2009 |
| WO | WO 2014/074529 | 5/2015 |
| WO | WO 2016/115487 | 7/2016 |

OTHER PUBLICATIONS

International Search Report and Written Opinion issued in International Patent Application No. PCT/US2018/056666, dated Jan. 2, 2019.
Yamagata, et al. "Targeting Th17 Effector Cytokines for the Treatment of Autoimmune Diseases," *Arch. Immunol. Ther. Exp.* (Warsz.), 2015, 63:405-414.
Brown et al. Cancer-associated bone disease. (2007) Cur. Osteopor. Rep. 5, 120-127.
Dias et al. The role of Th17/IL-17 on eosinophilic inflammation. (2013) J Autoimmun. 40:9-20.
International Preliminary Report on Patentability in International Application No. PCT/US2016/013645 dated Jul. 27, 2017.
Jin et al. Steps in prostate cancer progression that lead to bone metastasis. (2011) Int. J. Cancer 128, 2545-2561.
Junquera et al. Clinical experiences with bisphosphonate-associated osteonecrosis of the jaws: analysis of 21 cases. (2009) Am. J. Otolaryngol. 30(6), 390-395.
Kohno. Treatment of breast cancer with bone metastasis: bisphosphonate treatment—current and future. (2008) Int. J. Clin. Oncol. 13, 18-23.
Lecka, et al., "Nonhydrolyzable ATP Analogues as Selective Inhibitors of Human NPP1: A Combined Computational/Experimental Study," Journal of Medicinal Chemistry, 56(21), 8308-8320, 2013.
Mao, et al., "Synthesis of Novel Unsymetric Bisbenzimidazoles," Chinese Journal of Chemistry, 28(5), 818-824, 2010.
Nieto, et al., "Synthesis is Novel 1-alkyl-8-substituted-3-(3-Methoxypropyl) Xanthines as Putative A"2"B Receptor Antagonists," Bioorganic & Medicinal Chemistry, 17(9): 3426-3432, 2009.
Ouyang et al. The biological functions of T helper 17 cell effector cytokines in inflammation. (2008) Immunity. 28:454-467.
Paget. The Distribution of Secondary Growths in Cancer of the Breast. (1889) Lancet 133(3421), 571-573.
Partial Supplementary European Search Report Issued in Corresponding PCT Application No. 16737981.7, dated May 28, 2018.
Rapaport et al. Growth inhibition of human tumor cells in soft-agar cultures by treatment with low levels of adenosine 5'-triphosphate. (1983) Cancer Res. 43, 4402-4406.
Rapaport. Experimental cancer therapy in mice by adenine nucleotides. (1988) Eur. J. Cancer Clin. Oncol. 24, 1491-1497.
Roodman. Mechanisms of bone metastasis. (2004) N. Engl. J. Med. 350(16), 1655-1664.
Salvestrini et al. Purinergic signaling inhibits human acute myeloblastic leukemia cell proliferation, migration, and engraftment in immunodeficient mice. (2012) Blood 119, 217-226.
Shabbir et al. Purinergic receptor-mediated effects of adenosine 5'-triphosphate in urological malignant diseases (2009) Int. J. Urol. 16(2), 143-150.
Truong et al. Bisphosphonate-related osteonecrosis of the jaw presenting as a cutaneous dental sinus tract: A case report and review of the literature. (2010) J. Am. Acad. Dermatol. 62, 672-676.

(Continued)

*Primary Examiner* — Jeffrey H Murray

(57) ABSTRACT

Certain embodiments are directed to methods of treating autoimmune disorders by administering P2 purnergic receptor antagonist and/or adenosine receptor antagonists. The P2 purnergic receptor antagonist being chemical analogs of adenosine receptor antagonist 8-Ethoxy-9-ethyl-9H-purin-6-amine. The adenosine receptor antagonists being chemical analogs of the non-hydrolysable ATP analog adenosine 5'[γ-thio]triphosphate (ATPγS). Certain embodiments are directed to the use of the chemical analogs to modulate IL-17 activity.

7 Claims, No Drawings

(56) References Cited

OTHER PUBLICATIONS

Van der Pluijm et al. Monitoring Metastatic Behavior of Human Tumor Cells in Mice with Species-Specific Polymerase Chain Reaction: Elevated Expression of Angiogenesis and Bone Resorption Stimulators by Breast Cancer in Bone Metastases. (2001) J. Bone Miner. Res. 16, 1077-1091.

Wei, et al., "3D-Pharmacophore Models for Selective A2A and A2B Adenosine Receptor Antagonists," Journal of Chemical Information and Mode, American Cancer Society, 47(2):613-625, 2007.

Welch et al. Breast cancer metastasis to bone: Evolving models and research challenges. (2003) J. Musculoskelet. Neuronal Interact. 3, 30-38.

White et al. P2 receptors and cancer. (2006) Trends Pharmacol. Sci. 27(4), 211-217.

Yamagata et al. Targeting Th17 Effector Cytokines for the Treatment of Autoimmune Diseases. (2015) Arch. Immunol. Ther. Exp. (Warsz.) 63:405-414.

SMALL MOLECULES FOR THE TREATMENT OF AUTOIMMUNE DISORDERS

CROSS REFERENCE TO RELATED APPLICATIONS

This application is a national phase under 35 U.S.C. § 371 of International Application No. PCT/US2018/056666, filed Oct. 19, 2018, which claims the benefit of priority to U.S. Provisional Application Ser. No. 62/574,329, filed Oct. 19, 2017, the entire contents of each of which are incorporated here by reference in their entirety.

BACKGROUND

Autoimmunity is described as an immune response directed against an host antigen within the body of the host. This definition is independent of whether the response is innate or acquired, and if acquired whether it is induced by a foreign or autochthonous antigen. In other words, if acquired, the response is induced by a foreign antigen or antigen found in the part of the body or locality in which it originates, such as that produced by a cancer. Autoimmunity usually involves both T-cell and B-cell responses in a three dimensional complex immunologic array. The primary requirement is an immune response directed to a self-antigen.

In dealing with human disease it is often difficult to establish causality. As such the diagnosis of an autoimmune disease may be established by direct evidence, indirect evidence or circumstantial evidence. Direct evidence usually involves the transfer of an antibody from a patient to a healthy recipient. Indirect evidence can be found in such disease states as: (a) the reproduction of disease in animals via immunization with a select antigen, (b) naturally occurring disease in animals resembling the human counterpart, and (c) disease created by manipulating the immune system. Circumstantial evidence, the lowest level of proof, is suggested by confirming the presence of autoantibodies. Another type of circumstantial evidence is identified from the finding that autoimmune diseases have a tendency to cluster, likely from defined or yet to be defined genetic susceptibility traits. From a pathological perspective, with few exceptions, all autoimmune diseases require the presence of self-reactive CD4 T lymphocytes.

A separate category of autoimmune diseases, the autoinflammatory diseases, exists in which there is no evidence of adaptive immunity in the form of self-reactive T cells. This latter group consists of a core of six disorders known as hereditary recurrent fever syndromes.

Clinically, physicians tend to categorize autoimmune diseases as systemic (such as in the case of systemic lupus erythematosis) or organ-specific (such as type I diabetes mellitus). Therapy has generally been directed to the specific disease and associated presentation. Four therapeutic approaches are usually employed, but the complex causes of the two categories of autoimmune disorders offer considerable challenges to the development of new therapies. Moreover, many of the current modalities-such as the immunomodulators, immunosuppressants, steroids, and intravenous gamma globulin, to name a few-precipitate side effects that are worse than the underlying disease.

Autoimmune disease occurs when the body's immune system attacks healthy body tissue, which results in multiple disorders including rheumatoid arthritis, multiple sclerosis and inflammatory bowel disease (Ouyang et al., 2008, *Immunity*, 28:454-67). The activation of IL-17 pathway is a major mechanism for the development of these autoimmune diseases. IL-17 is a cytokine produced and secreted primarily by CD4+ T cells (Th17) and also by other lymphocytes. Published studies show that IL-17 is greatly increased at sites of inflammatory tissues of autoimmune diseases and amplifies the inflammation (Dias and Banerjee, 2013, *J Autoimmun.* 40:9-20). In addition, purinergic receptor signaling regulated by ATP or adenosine is also shown to regulate the secretion of IL-17. Therefore, targeting and inhibiting IL-17 inhibitors is considered as a key strategy for the treatment of these autoimmune diseases (Yamagata et al., 2015, *Arch. Immunol. Ther. Exp.* (Warsz.) 63:405-14).

There remains a need for additional treatments for autoimmune disorders.

SUMMARY

The inventors have identified purinergic receptor antagonist/agonist for inhibition of IL-17 secretion by 45-65%. Given these results, these purinergic receptor antagonist/agonist can be used for the treating autoimmune disorder. In certain aspects the autoimmune disorder is rheumatoid arthritis, multiple sclerosis, or inflammatory bowel disease.

Certain embodiments are directed to non-hydrolysable ATP analog, e.g., P2 purinergic receptor antagonist, that modulate IL-17 activity. The term non-hydrolysable ATP analog refers to an ATP analog that is not effectively hydrolyzed by ATPase, if at all, at a rate that is less than 5, 1, or 0.1% of the rate of ATP hydrolysis by ATPase. Certain embodiments are directed to various chemical analogs of the non-hydrolysable ATP analog adenosine 5'-[γ-thio]triphosphate (ATPγS), e.g., P2 purinergic receptor antagonist. Certain embodiments are directed to P2 purinergic receptor antagonist having the general formula of Formula: I, including compounds P1-P6 (Table 1)

Formula I

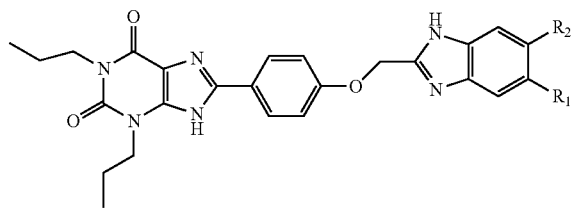

where $R_1$ and $R_2$ are selected independently from hydrogen (H), cyano (CN), C1 to C3 alkyl, halogen (fluoro (F), chloro (Cl), bromo (Br), or iodo (I)), or a trifluoromethyl ($CF_3$). In certain aspects $R_1$ is selected from hydrogen, cyano, C1 to C3 alkyl, halogen (fluoro (F), chloro (Cl), bromo (Br), or iodo (I)), or a trifluoromethyl, and $R_2$ is hydrogen or fluoro. In a further aspect $R_1$ is cyano and $R_2$ is H, $R_1$ is H and $R_2$ is H, $R_1$ is trifluoromethyl and $R_2$ is H, $R_1$ is fluoro and $R_2$ is H, $R_1$ is methyl and $R_2$ is H, and $R_1$ is fluoro and $R_2$ is fluoro.

Certain embodiments are directed to administration of one or more compounds of Formula I to modulate IL-17 or treat autoimmune disorders. The compounds can be administered alone or in combination with other therapies.

Adenosine exposure can modulate IL-17 activity, and adenosine is produced by the metabolism of ATP. Certain embodiments are directed to a number of chemical analogs of adenosine receptor antagonist 8-Ethoxy-9-ethyl-9H-purin-6-amine (ANR94, A2A antogonist). These compounds are inhibitors of IL-17 activity. In certain aspects the chemical analogs of adenosine receptor antagonist 8-Ethoxy-9-ethyl-9H-purin-6-amine have a general formula of Formula II, including compounds P7-P10 (Table 1)

Formula II

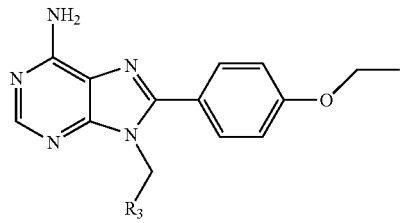

Certain aspects are directed to compounds of Formula II, where $R_3$ is selected from dihalomethyl, C3 to C5 cycloalkyl, or tetrahydrofuran. In certain aspects $R_3$ is difluoromethyl, cyclopropyl, cyclobutyl, or β-tetrahydrofuran.

Certain embodiments are directed to administration of one or more compounds having a formula of Formula II to treat an autoimmune disorder. The compounds can be administered alone or in combination with compounds with Formula I and/or other therapies.

In certain aspects one or more compounds having a formula of Formula I and/or Formula II are administered to a subject in need of treatment for an autoimmune disorder. In certain aspects the compounds of Formula I and/or Formula II are administered within 1, 5, 10, 20, 30, or 60 minutes or hours of each other. In a further aspect the compounds are administered concurrently. In another aspect one or more compounds of Formula I are administered before, during, or after administration of one or more compounds of Formula II.

TABLE 1

List of representative compounds

| Compound Code | Structure |
|---|---|
| P1 | 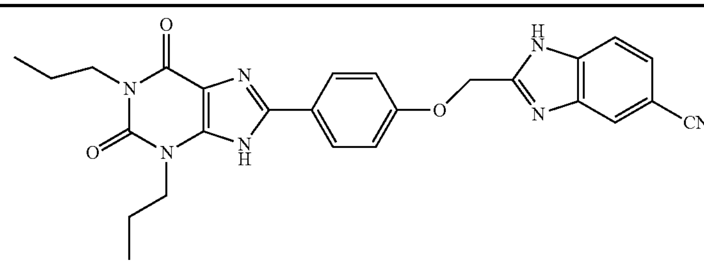 |
| P2 | 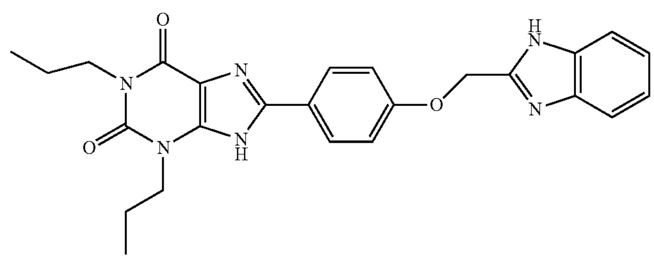 [SMILES: CCCn1c(=O)c2nc(-c3ccc(OCc4nc5ccccc5[nH]4)cc3)[nH]c2n(CCC)c1=O] |
| P3 | 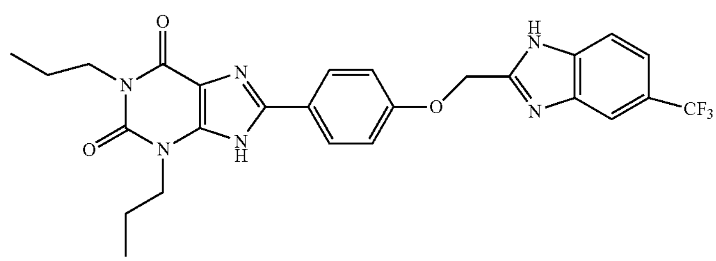 [SMILES: CCCn1c(=O)c2nc(-c3ccc(OCc4nc5cc(C(F)(F)F)ccc5[nH]4)cc3)[nH]c2n(CCC)c1=O] |

TABLE 1-continued

List of representative compounds

| Compound Code | Structure |
|---|---|
| P5 | 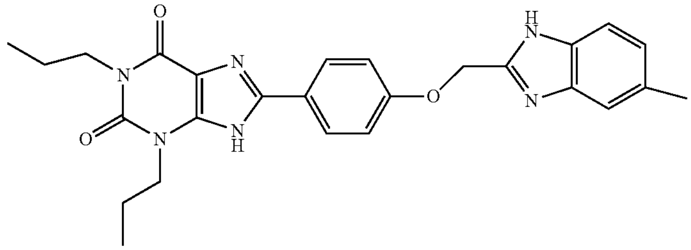 [SMILES: CCCn1c(=O)c2nc(-c3ccc(OCc4nc5cc(C)ccc5[nH]4)cc3)[nH]c2n(CCC)c1=O] |
| P6 | 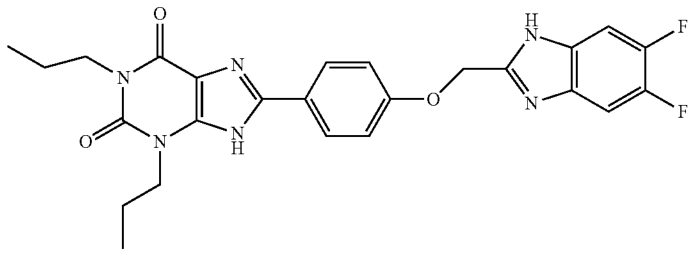 [SMILES: CCCn1c(=O)c2nc(-c3ccc(OCc4nc5cc(F)c(F)cc5[nH]4)cc3)[nH]c2n(CCC)c1=O] |
| P7 | 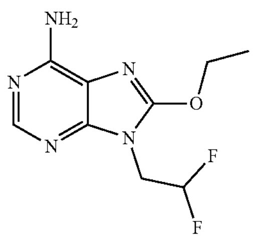 [SMILES: CCOc1nc2c(N)ncnc2n1CC(F)F] |
| P8 | 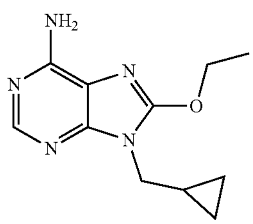 [SMILES: CCOc1nc2c(N)ncnc2n1CC1CC1] |
| P9 | 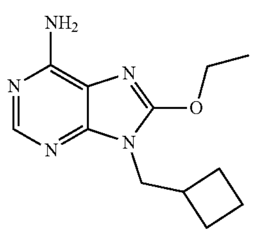 [SMILES: CCOc1nc2c(N)ncnc2n1CC1CCC1] |
| P10 | 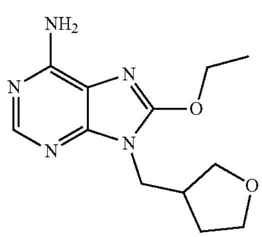 [SMILES: CCOc1nc2c(N)ncnc2n1CC1CCOC1] |

TABLE 2

Inhibition of IL-17 Secretion by compounds.

| Compounds | IL-17 Secretion Inhibition |
|---|---|
| P2 | 54.1% |
| P5 | 64.3% |
| P8 | 45.4% |

In certain aspects a subject or patient has rheumatoid arthritis, multiple sclerosis, inflammatory bowel disease, or another autoimmune disorder.

In certain embodiments bisphosphonate drugs can be explicitly excluded from the claimed invention due to their potential in vivo toxicity.

As used herein, an "inhibitor" can be a chemical compound that can reduce the activity or function of a protein. An inhibitor, for example, can inhibit directly or indirectly the activity of a protein. Direct inhibition can be accomplished, for example, by binding to a protein and thereby preventing the activity of the protein, or by inhibiting an enzymatic or other activity of the protein competitively, non-competitively, or uncompetitively. Indirect inhibition can be accomplished, for example, by binding to a protein's intended target, such as a receptor or binding partner, thereby blocking or reducing activity of the protein; or by modulating the expression of the protein.

The term "effective amount" includes an amount effective, at dosages and for periods of time necessary, to achieve the desired result, e.g., sufficient to treat autoimmune disorder. An effective amount of a P2 purinergic receptor antagonist and/or adenosine receptor antagonist may vary according to factors such as the disease state, age, and weight of the subject, and the ability of P2 purinergic receptor antagonist and/or adenosine receptor antagonists to elicit a desired response in the subject. Dosage regimens may be adjusted to provide the optimum therapeutic response. An effective amount is also one in which any toxic or detrimental effects (e.g., side effects) of P2 purinergic receptor antagonist and/or adenosine receptor antagonists are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with P2 purinergic receptor antagonist and/or adenosine receptor antagonists, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent or it may be variable at relevant times during or after P2 purinergic receptor antagonist and/or adenosine receptor antagonists are administered to a subject or is used in an assay or other method described herein, e.g., within timeframes described infra, or about 1 hour after the administration or use of P2 purinergic receptor antagonist and/or adenosine receptor antagonists to about 28 days, or 1, 3, 6, 9 months or more after a subject(s) has received such treatment.

The "modulation" of, e.g., a symptom, level or biological activity of a molecule (e.g., IL-17), or the like, refers, for example, to the symptom or activity, or the like that is detectably increased or decreased. Such increase or decrease may be observed in treated subjects as compared to subjects not treated with P2 purinergic receptor antagonist and/or adenosine receptor antagonists, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after P2 purinergic receptor antagonist and/or adenosine receptor antagonists are administered to a subject or is used in an assay or other method described herein or a cited reference, e.g., within times described infra, or about 1 hour after the administration or use of P2 purinergic receptor antagonist and/or adenosine receptor antagonists to about 3, 6, 9 months or more after a subject(s) has received P2 purinergic receptor antagonist and/or adenosine receptor antagonists.

As used herein, the terms "prevent," "preventing," and "prevention" refer to the prevention of the recurrence, onset, or development of an autoimmune disorder. Preventing includes protecting against the occurrence and severity of upper and/or lower respiratory tract infections, as well as other autoimmune disorders.

As used herein, the term "prophylactically effective amount" refers to the amount of a therapy (e.g., a pharmaceutical composition comprising P2 purinergic receptor antagonist and/or adenosine receptor antagonists) which is sufficient to result in the prevention of the development, recurrence, or onset of autoimmune disorders or to enhance or improve the prophylactic effect(s) of another therapy.

As used herein, "subject" includes organisms which are capable of suffering from autoimmune disorders or other disorder treatable by a combination of P2 purinergic receptor antagonist and/or adenosine receptor antagonists or who could otherwise benefit from the administration of P2 purinergic receptor antagonist and/or adenosine receptor antagonists as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION

Certain embodiments are directed to methods and compositions for treating autoimmune disorders.

Autoimmunity is described as an immune response directed against an antigen within the body of the host. This definition is independent of whether the response is innate or acquired, and if acquired, whether it is induced by a foreign or autochthonous antigen. In other words, if acquired, the response is induced by a foreign antigen or antigen found in the part of the body or locality in which it originates. Autoimmunity usually involves both T-cell and B-cell responses in a three dimensional complex immunologic array. The primary requirement is an immune response directed to a self-antigen.

In dealing with human disease it is often difficult to establish causality. As such the diagnosis of an autoimmune disease may be established by direct evidence, indirect evidence or circumstantial evidence. Direct evidence usually involves the transfer of an antibody from a patient to a healthy recipient. Examples are the reproduction of the disease pemphigus by injection of patient serum into a neonatal mouth or human-to-human transfer of an autoantibody from the transplacental migration of the disease, e.g., Grave's disease, myasthenia gravis, and neonatal lupus. Indirect evidence can be found in such disease states as: (a) the reproduction of disease in animals via immunization with a select antigen, (b) naturally occurring disease in animals resembling the human counterpart, and (c) disease created by manipulating the immune system.

From a pathological perspective, with few exceptions all autoimmune disorders require the presence of self-reactive CD4 T lymphocytes, and can include, but not limited to Multiple sclerosis, Sympathetic opthalmia, Graves' disease, Hashimoto's thyroiditis, Goodpasture's syndrome, Pernicious anemia, Crohn's disease, Ulcerative colitis, psoriasis, ankylosing spondylitis, Diabetes mellitus type I, Immune thrombocytopenia, Myasthenia gravis, Hemolytic anemia, Sjögren's syndrome, Rheumatoid arthritis, Wegener's granulomatosis, Systemic lupus erythematosus, and the like. In certain aspects the autoimmune disorder is a spondyloarthropathies. The Spondyloarthropathies (SpA) are an important group of chronic inflammatory disorders, affecting both the axial and peripheral skeleton. Within the SpA group, several entities are recognized: Ankylosing Spondylitis (AS), Psoriatic Arthritis (PsA), Enteropathic Arthritis or Arthritis associated with inflammatory bowel disease (IBD-SpA), Reactive Arthritis (ReA) including Reiter's syndrome and the undifferentiated forms (UspA) and, possibly, also Whipple disease and Behcet disease.

Certain embodiments are directed to compounds having a chemical formula of Formula I, for example P1, P2, P3, P4, P4, P5, or P6 (Table 1).

Other embodiments are directed to compounds having a chemical formula of Formula II, for example P7, P8, P9, or P10, which are chemical analogs of adenosine receptor antagonist 8-Ethoxy-9-ethyl-9H-purin-6-amine (ANR94, A2A antagonist) (Table 1). At 50 µM, none of the compounds exerted any toxicity to the cell.

In certain aspect compounds having Formula I and/or Formula II (e.g., compounds P1-P10) can be used to treat autoimmune disorders. In certain aspects the autoimmune disorder is has rheumatoid arthritis, multiple sclerosis, or inflammatory bowel disease.

In certain embodiments, the invention also provides compositions comprising one or more compound having the chemical formula of Formula I and/or Formula II (e.g., P1-P2) in a pharmaceutically acceptable formulation. Thus, the use of one or more compound described herein in the preparation of a medicament is also included. Such compositions can be used in the treatment of a variety of autoimmune disorders.

The compounds described herein may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the compounds described herein, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. When administering the compositions by injection, the administration may be by continuous infusion or by single or multiple boluses. For parenteral administration, the agents may be administered in a pyrogen-free, parenterally acceptable aqueous solution comprising the desired compound in a pharmaceutically acceptable vehicle. A particularly suitable vehicle for parenteral injection is sterile distilled water in which one or more therapeutic agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under good manufacturing practice (GMP) conditions.

For the compounds described herein, alone or as part of a pharmaceutical composition, such doses are between about 0.001 mg/kg and 1 mg/kg body weight, preferably between about 1 and 100 μg/kg body weight, most preferably between 1 and 10 μg/kg body weight. In certain aspects, compounds described herein can be administered by infusion to patients in daily dosages at rates ranging from 20, 25, 30, 35, 40 to 30, 35, 40, 45, 50 μg/kg/min (including all values and ranges there between) for up to 8 hours, including 1, 2, 3, 4, 5, 6, 7, or 8 hours. Compounds described herein can be administered orally at about 1, 10, 20, 30, 40, 50, 60 to 50, 60, 70, 80 90, 100 μg/kg or mg/kg of body weight per day. In certain aspects the compounds described herein can be administered at about 0.01 to 10 mg/kg of body weight per day.

Therapeutically effective doses will be easily determined by one of skill in the art and will depend on the severity and course of the disease, the patient's health and response to treatment, the patient's age, weight, height, sex, previous medical history and the judgment of the treating physician.

In additional embodiments, patients may also be administered directly, endoscopically, intratracheally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes. Methods of the invention can be used in conjunction with these known anti-inflammation therapies.

Various chemical definitions related to such compounds are provided as follows.

As used herein, the term the term "fluro" designates —F; the term "cyano" means —CN; the term "methyl" means —$CH_3$; the term "diflouromethyl" means —$CF_2H$; the term "triflurometyl" means —$CF_3$; the term "cyclopropyl" means a three membered saturated cycloalkyl ring; the term "cyclobutyl" means four membered saturated cycloalkyl ring; and the term "β-tetrahydrofuran" means a five membered saturated heterocyclyl ring with O as heteroatom and is substituted at the β carbon from the heteroatom.

As used herein, the term "halo" designates —F, —Cl, —Br or —I; the term "mercapto" means —SH; the term "cyano" means —CN; the term "azido" means —$N_3$; and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$ (Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkyl sulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —NH($C_{1-4}$alkyl), —N($C_{1-4}$alkyl)$_2$, —$NO_2$, —S($C_{1-4}$alkyl), —$SO_2$($C_{1-4}$alkyl), —$CO_2$($C_{1-4}$alkyl), and —O($C_{1-4}$alkyl).

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

It is contemplated that any embodiment discussed in this specification can be implemented with respect to any method or composition of the invention, and vice versa. Furthermore, compositions of the invention can be used to achieve methods of the invention.

The invention claimed is:

1. A method for modulating IL-17 secretion comprising administering to a patient having or at risk of having an autoimmune disorder an effective amount of a one or more compounds selected from:
   (a) a P2 purnergic receptor antagonist with general formula of Formula I

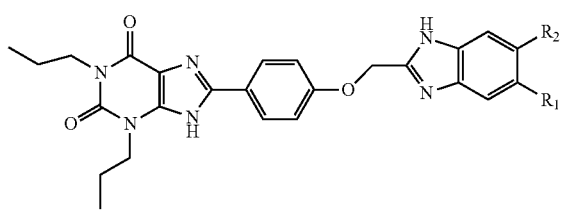

Formula I where $R_1$ and $R_2$ are independently selected from hydrogen, cyano, C1 to C3 alkyl, halo, or heteromethyl; or
   (b) a chemical analog of adenosine receptor antagonist 8-Ethoxy-9-ethyl-9H-purin-6-amine with general formula of Formula II

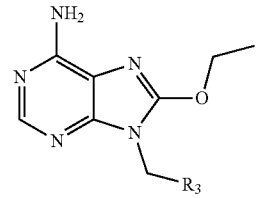

Formula II where $R_3$ is a heteromethyl, cycloalkyl, or tetrahydrofuran.

2. The method of claim 1, wherein the one or more compounds are administered intravenously.

3. The method of claim 1, wherein the one or more compounds of are administered orally.

4. The method of claim 1, wherein $R_1$ is selected from hydrogen, cyano, C1 to C3 alkyl, halo, or heteromethyl, and $R_2$ is a hydrogen or halogen.

5. The method of claim 1, wherein $R_1$ is a hydrogen, fluoro, methyl, cyano, or trifluoromethyl.

6. The method of claim 1, wherein $R_1$ is cyano and $R_2$ is hydrogen, $R_1$ is hydrogen and $R_2$ is hydrogen, $R_1$ is trifluoromethyl and $R_2$ is hydrogen, $R_1$ methyl and $R_2$ is hydrogen, or $R_1$ is fluoro and $R_2$ is fluoro.

7. The method of claim 1, wherein $R_3$ is difluoro methyl, cyclopropyl, cyclobutyl, or β-tetrahydrofuran.

* * * * *